US008323193B2

(12) United States Patent
Skerl et al.

(10) Patent No.: US 8,323,193 B2
(45) Date of Patent: Dec. 4, 2012

(54) IMPLANTABLE BIOSENSOR AND SENSOR ARRANGEMENT

(75) Inventors: Olaf Skerl, Bad Doberan (DE); Albrecht Urbaszek, Heroldsbach (DE); Gerald Czygan, Buckenhof (DE)

(73) Assignee: Biotronik CRM Patent AG, Baar (CH)

( * ) Notice: Subject to any disclaimer, the term of this patent is extended or adjusted under 35 U.S.C. 154(b) by 632 days.

(21) Appl. No.: 12/541,091

(22) Filed: Aug. 13, 2009

(65) Prior Publication Data

US 2010/0056888 A1    Mar. 4, 2010

(30) Foreign Application Priority Data

Aug. 27, 2008    (DE) .......................... 10 2008 039 858

(51) Int. Cl.
    *A61B 5/00* (2006.01)
(52) U.S. Cl. ........................ 600/309; 600/365
(58) Field of Classification Search .................. 600/345, 600/347, 309, 365; 310/313
    See application file for complete search history.

(56) References Cited

U.S. PATENT DOCUMENTS

| | | | | |
|---|---|---|---|---|
| 5,212,988 | A * | 5/1993 | White et al. | 73/599 |
| 5,306,644 | A * | 4/1994 | Myerholtz et al. | 436/149 |
| 6,407,479 | B1 * | 6/2002 | Moellendorf et al. | 310/313 A |
| 6,475,750 | B1 * | 11/2002 | Han et al. | 435/14 |
| 7,017,416 | B1 * | 3/2006 | Liu et al. | 73/702 |
| 7,205,701 | B2 * | 4/2007 | Liu et al. | 310/313 R |
| 7,399,280 | B2 * | 7/2008 | Liu et al. | 600/504 |
| 7,556,775 | B2 * | 7/2009 | McGill et al. | 422/88 |
| 2004/0045879 | A1 | 3/2004 | Shults et al. | |
| 2004/0072208 | A1 * | 4/2004 | Warthoe et al. | 435/6 |
| 2005/0061079 | A1 | 3/2005 | Schulman | |
| 2006/0049714 | A1 * | 3/2006 | Liu et al. | 310/313 R |
| 2006/0258761 | A1 | 11/2006 | Boock et al. | |
| 2007/0113658 | A1 * | 5/2007 | Combi et al. | 73/702 |
| 2007/0190662 | A1 * | 8/2007 | Baetzold et al. | 436/166 |
| 2007/0236213 | A1 * | 10/2007 | Paden et al. | 324/228 |

(Continued)

FOREIGN PATENT DOCUMENTS

WO    2009025563 A1    2/2009

OTHER PUBLICATIONS

"A MEMS Viscometric Sensor for Continuous Glucose Monitoring." Zhao et al. J. Micromech. Microeng. 17 (2007) 2528-2537.*
"Surface Acoustic Wave Biosensors: A Review." Länge et al. Anal Bioanal Chem. Jul. 2008;391(5):1509-19. Epub Feb. 12, 2008.*

(Continued)

*Primary Examiner* — Michael Kahelin
*Assistant Examiner* — Meredith Weare
(74) *Attorney, Agent, or Firm* — Arc IP Law, PC; Joseph J. Mayo (57) ABSTRACT

An implantable biosensor, which comprises a measuring (or first) chamber filled with the test fluid, which is able to convert a change of the concentration of a predetermined analyte or ion type into a change of a physical variable. To this end, the measuring chamber is closed by at least one membrane, which is permeable to the analyte or ion type and impermeable to the test fluid. In addition, the biosensor is equipped with at least one microacoustic sensor, which is operatively connected to the test fluid such that it can detect the physical variable that changes with the concentration of the analyte or ion type. Further relates to a sensor arrangement comprising at least one such implantable biosensor, the arrangement including a polling system that is wirelessly coupled to the biosensor.

5 Claims, 5 Drawing Sheets

U.S. PATENT DOCUMENTS

| | | | |
|---|---|---|---|
| 2007/0282172 A1* | 12/2007 | Toumazou et al. | 600/300 |
| 2008/0100176 A1* | 5/2008 | Haskell et al. | 310/313 R |
| 2008/0202657 A1* | 8/2008 | Hammel | 152/152.1 |
| 2009/0025459 A1* | 1/2009 | Zhang et al. | 73/54.41 |
| 2009/0191642 A1* | 7/2009 | Wang et al. | 436/95 |
| 2011/0124985 A1* | 5/2011 | Meurville et al. | 600/309 |

OTHER PUBLICATIONS

Karilainen et al. "Mobile Patient Monitoring Based on Impedance-Loaded SAW-Sensors." IEEE Trans Ultrason Ferroelectr Freq Control. Nov. 2004;51(11):1464-9.*

"Acoustic Wave Sensors." Ventron International. Nov. 8, 2006. 44 pages.*

Lange et al., "Influence of intermediate aminodextran layers of the signal response of surface acoustic wave biosensors" Analytical Biochemistry 377 (2008) 170-175.

European Search Report received for EP Application No. 09166549.7, dated Jan. 20, 2012, 10 pages.

European Search Report received for EP Application No. 09166549.7, dated Mar. 26, 2012, 14 pages.

* cited by examiner

IMPLANTABLE BIOSENSOR AND SENSOR ARRANGEMENT

This application takes priority from German Patent Application DE 10 2008 039 858.6, filed 27 Aug. 2008, the specification of which is hereby incorporated herein by reference.

BACKGROUND OF THE INVENTION

1. Field of the Invention

The invention is in the field of sensor technology and relates to an implantable, wirelessly readable biosensor and to a sensor arrangement equipped with such a biosensor.

2. Description of the Related Art

A wide variety of an analytical methods and the necessary device technology therefore exists for detecting the presence of analytes and determining the concentrations thereof in bodily fluids, such as blood. In general, fluid samples are collected, which optionally may be specially conditioned and then supplied to the analysis. The spectrum ranges from simple test strips, which indicate the presence and the concentration of a specific substance (such as glucose) for example by a color change, to complex analyses in specialized laboratories. A key disadvantage of these methods is that samples are collected only a certain (discrete) times and are then analyzed in a more or less complex manner. Particularly with laboratory analyses, additionally the time period between sampling and the availability of the result is usually quite long. In this way, continuous measurements are not possible with these methods.

Often, continuous measurement is desirable, particularly if the measured values are to be used for managing medical devices. By way of example of a disease where continuous measurement is advantageous Diabetes mellitus shall be mentioned. Diabetes mellitus is a wide-spread disease with approximately 250 million cases worldwide, which corresponds to approximately 6% of the worldwide population. Complications and secondary diseases frequently occur in connection with Diabetes mellitus. One example of this is heart disease, which occurs with greater frequency in people with Diabetes mellitus. The therapy of Diabetes mellitus usually is performed by administering insulin, for which a measurement of the blood sugar level is required. The more frequently the blood sugar level is measured, the more efficiently the therapy can be. Automatic insulation administration, for example using insulin pumps, requires a continuous measurement of the blood sugar level in order to enable optimized insulin dosages that are in keeping with the patient's needs.

Furthermore, continuous monitoring of the concentrations of enzymes, hormones, marker molecules, pH values, or of glucose concentrations, is desirable in order to detect pathological changes at an early stage and be able to initiate the necessary therapies.

For this reason, biosensors have attained great importance in the detection of enzymes, hormones, marker molecules, pH values, or glucose concentrations. Chemical and biological sensors are based on the fundamental principle of selectively converting the concentration or the presence of a certain substance into the change of a physical variable, which then can be measured electrically, for example. These physical variables, for example, can be the wavelength of absorbed or emitted light, pressure, viscosity, mass, or also electric variables such as currents, voltages, or impedances.

One possibility for the implementation of sensors are hydrogels. Hydrogels are special polymers, which are able to absorb a solvent, for example water, in a volume that is several times that of their own. This property is created by linking the polymer molecules into a three-dimensional network, into which the solvent molecules (such as water) can become incorporated. Hydrogels can be designed such, for example, that they respond to the change of the concentrations of certain ions (such as the pH value) or certain substances (such as glucose or hormones) with relatively large volume changes. It is also possible to specifically embed compounds that have an affinity for certain substances (such as concanavalin A for glucose) in order to influence in this way the properties of the hydrogel as a function of the concentration of this substance. Beyond the volume change, during the incorporation of the solvent, for example, the viscosity, density, and/or optical and electric properties of the hydrogels can also change. Due to this behavior, hydrogels are suited as a basis for biosensors and chemical sensors. The measurement performed relates to the change of a certain property of the hydrogel (for example the viscosity thereof) in order to determine a concentration of the substance to be determined.

A person skilled in the art is furthermore familiar with so-called SAW (SAW=Surface Acoustic Wave) sensors. SAW sensors in general comprise a piezoelectric substance, to the surface of which so-called interdigital electrodes (IDT=Inter Digital Transducer) are applied. If an AC voltage is applied to an IDT ("input IDT"), acoustic surface waves are generated by way of the inverse piezo effect, which can propagate across the surface of the substrate. These surface waves can be reflected on one or more acoustic reflectors (such as an IDT) and then generate an AC voltage in the input IDT by way of the piezo effect. For example, if an AC voltage pulse is coupled into the input IDT via an antenna, it is converted into an acoustic wave package, which after reflection on the acoustic reflector generates an AC voltage pulse in the input IDT, which is emitted via said antenna, similar to an echo. No additional energy is required for returning this echo. SAW sensors can be configured as delay lines or as so-called one-port resonators and can be operated with frequencies from approximately 30 MHz to more than 10 GHz.

The propagation of the acoustic wave on the surface of the substrate is influenced by different factors, such as the mechanical stress in the substrate, the temperature, the ground layer on the surface, or the acoustic coupling to the ambient medium. As a result of these influences, among other things the propagation velocity of the acoustic surface waves or the attenuation thereof changes, thereby changing the properties of the echo, for example the travel time or amplitude.

Due to these properties, it is possible by means of SAW sensors to implement purely passive, wirelessly readable sensors for different physical variables, which can be polled using a high-frequency electromagnetic pulse, comparable to a radar pulse. The echo received contains the information about the measured value.

SAW sensors can be used as pressure sensors, for example. To this end, the substrate is applied onto a membrane, for example, whereby it is slightly deflected. This deflection can also be achieved in that the force is transmitted from the membrane via a tappet to the suitably supported substrate. Due to the deflection of the substrate, mechanical stresses develop therein, which influence, for example, the propagation velocity of the acoustic wave. As a result, the resonant frequency of the SAW sensor or the phasing of the echo relative to the exciting pulse changes as a function of the mechanical stress, and consequently as a function of the pressure to be measured.

SAW sensors are likewise well-suited for measuring the viscosity of fluids. Here, primarily SAW arrangements are used which operate based on acoustic shear waves (SHwaves). Shear waves have the advantage that acoustically they couple to the fluid only via the viscosity and therefore the attenuation of the surface wave by the adjoining fluid is relatively low. The penetration depth (d) of the surface wave into the fluid depends on the viscosity (η) thereof, the density (ρ) thereof, and the frequency of the surface wave (ω):

$$d = \sqrt{\frac{2\eta}{\omega\rho}}.$$

Coupling of the acoustic wave into the fluid therefore effectively results in mass loading of the surface, as a result of which the propagation velocity of the acoustic surface wave changes, and also in an attenuation of the wave. These effects can be expressed by acoustic impedance ($Z_a$) of the fluid, which likewise depends on the viscosity (η), density (ρ) and frequency (ω)

$$Z_a = \sqrt{\omega\rho\eta}.$$

As a result, the resonant frequency of the SAW sensor, the phasing of the echo relative to the exciting pulse, or the amplitude of the echo changes as a function of the viscosity of the coupled fluid.

SAW sensors are also suited for measuring conductivities and impedances. For this purpose, the ports of one of the acoustic reflectors on the surface of the SAW sensor are electrically connected to the impedance to be measured, for example electrodes disposed in a defined manner in a fluid. This acoustic reflector is thereby loaded by the electric impedance ($Z=R+jX$) of the electrode arrangements. As a result, the amplitude and phasing of the echo of this reflector change as a function of the magnitude and phase of the electric impedance of the electrode arrangement, which is influenced both by the electric conductivity of the fluid and by the dielectric properties thereof. The decay behavior of the SAW sensor is also influenced by the load impedance, for example the decay time constant thereof. In this way, the electric properties of the fluid, for example the conductivity or dielectric constant thereof, can be measured by the determination of the parameters of the echoes received.

SAW sensors according to the principles described have already proven useful in industrial applications, for example as tire pressure sensors or oil quality sensors.

As continuously measuring methods, applications based on SAW sensors are known in which the mass accumulation of specific substances is measured. To this end, the surface of the SAW sensor is coated with a selective material, on which the analyte accumulates. The increase in mass on the surface of the SAW sensor is measured using generally known methods and is used to determine the presence and concentration of the analyte. A frequent disadvantage of this method is that the selective coating ages, becomes contaminated, or the absorption of the analyte is not reversible, so that after a certain usage period the measurement is not longer possible with sufficient accuracy and the SAW sensors have to be replaced.

In order to overcome the disadvantage of a short usage period, arrangements are known which operate based on hydrogels. For example, the viscosity of a hydrogel changes upon the penetration of an analyte (such as glucose) into the polymer matrix. The advantage is that this process reversible. With a suitable arrangement, a variable concentration balance develops between the test fluid (hydrogel) and the surrounding area. By measuring the viscosity change, the concentration of the analyte in the sample fluid can be determined (affinity viscosimetry). For example, the viscosity can be measured by the flow resistance over a capillary through which fluid flows. The disadvantage here is that a flow in the sensitive fluid (or hydrogel) must be driven and that the sensitive fluid is consumed in some arrangements. These methods are primarily suited for laboratory measurements. Arrangements in which the viscosity is determined by way of the oscillation behavior of a bending beam enclosed by the hydrogel are not associated with this disadvantage. However, a relatively large amount of energy is required for the excitation of the oscillations of the bending beam, the measurement thereof, and the transmission of the measured values via a telemetry connection, so that the service life and the size of an implantable sensor according to this principle are determined by the battery capacity thereof. Otherwise, energy must be transmitted from the outside for operating the sensor, wherein the sensor then has to comprise means for receiving and storing this energy.

Furthermore arrangements are known which utilize the volume changes of hydrogels by the incorporation of an analyte for determining the concentration. The hydrogel is then provided in a capsule that is closed with a firm semi-permeable membrane. The swelling of the hydrogel effects the pressure change in this capsule, which is measured by means of any arbitrary pressure pickup. Likewise, the osmotic pressure developing as a result of the difference in concentrations inside and outside the capsule can be used for determining the concentration of the analyte. The signals of the pressure pickup are processed in the sensor by measuring electronics and actively transmitted via a telemetry connection. The energy required for this again has to be provided by a battery or by energy transmission. Other known implantable sensors used for determining the concentration of an analyte, for example in the form of a stent, also have the disadvantage that they require a battery or a possibility for energy transmission for operating the measuring electronics and for active telemetry.

BRIEF SUMMARY OF THE INVENTION

It is desirable to implement an implantable, purely passive sensor that can be read wirelessly using electromagnetic pulses for determining the concentration of an analyte, such as glucose, in bodily fluids. The size and the service life of the sensor are not limited by the size of the battery or energy accumulator and the measuring electronics.

These and other objects are achieved according to the concept of the invention by an implantable biosensor and a sensor arrangement having the characteristics of the independent claims. Advantageous embodiments of the invention are provided by the characteristics of the dependent claims.

According to a first concept of the invention, an implantable, wireless or wirelessly readable biosensor for medical use is provided. The biosensor comprises a measuring chamber filled with a test fluid. The test fluid is able to convert a change of the concentration of a predetermined analyte or ion type into a change of a physical variable. Preferably, it is a hydrogel. The measuring chamber is closed by at least one so-called semi-permeable membrane, which is to say the membrane is permeable to the predetermined analyte or ion type and impermeable to the test fluid. In addition, the biosensor is equipped with at least one microacoustic sensor, for example a SAW sensor, which is operatively connected or coupled to the test fluid such that it can detect the physical variable of the test fluid that changes with the concentration of the predetermined analyte or ion type.

Here and hereinafter, a "microacoustic sensor" shall be understood as a sensor, which can convert an electromagnetic pulse into an acoustic wave, and/or an acoustic wave into an electromagnetic pulse. In particular, it can be a SAW sensor described above.

In an advantageous first embodiment of the implantable biosensor, it comprises a first chamber filled with the test fluid and a second chamber not filled with the test fluid. To this end, a first microacoustic sensor, for example a SAW sensor, is accommodated in the first chamber and operatively connected to the test fluid such that it can detect the physical variable that changes with the concentration of the predetermined analyte or ion type. In addition, a second microacoustic sensor, for example a SAW sensor, is accommodated in the second chamber, can detect the temperature in the second chamber and serves as a reference sensor.

In this embodiment of the implantable biosensor, it can be advantageous if the first microacoustic sensor can detect the viscosity of the test fluid, wherein the test fluid in particular may be designed such that it can convert a change of the concentration of an analyte, in particular glucose, into a change of the viscosity thereof.

In an advantageous second embodiment of the implantable biosensor, it comprises a first chamber filled with the test fluid and a second chamber not filled with the test fluid, wherein the two chambers are separated from each other at least in some sections by a first pressure measuring membrane, which deforms in the event of a pressure difference between the two chambers. In addition, the second chamber is separated at least in some sections from the surrounding area by a second pressure measuring membrane, which deforms in the event of a pressure difference of the second chamber relative to the surrounding area. Here, a microacoustic sensor, such as a SAW sensor, is accommodated in the second chamber and operatively connected or coupled to the two pressure measuring membranes such that it can detect the deformations thereof.

In an advantageous third embodiment of the implantable biosensor, it comprises a first chamber filled with the test fluid and a second chamber not filled with the test fluid, wherein the two chambers are separated from each other at least in some sections by a first pressure measuring membrane, which deforms in the event of a pressure difference between the two chambers. In addition, the second chamber is separated from the surrounding area at least in some sections by a second pressure measuring membrane, which deforms in the event of a pressure difference of the second chamber relative to the surrounding area. Here, a first microacoustic sensor and a second microacoustic sensor are each accommodated in the second chamber, wherein the first microacoustic sensor is operatively connected or coupled to the first pressure measuring membrane such that it can detect the deformation thereof, and the second microacoustic sensor is operatively connected or coupled to the second pressure measuring membrane such that it can detect the deformation thereof.

In the second and third embodiments of the biosensor according to the invention, it may be advantageous if the microacoustic sensor is configured as a bendable element that is mechanically coupled to the operatively connected pressure measuring membrane, for example in the form of a bending beam.

In the second and third embodiments of the biosensor according to the invention, it may furthermore be advantageous if a (where necessary, additional) microacoustic sensor is accommodated in the second chamber and can detect the temperature.

In the second and third embodiments of the biosensor according to the invention, it may additionally be advantageous if the test fluid is designed such that it can convert a change of the concentration of an analyte, particularly glucose, or an ion type into a change of the volume of the fluid.

In an advantageous fourth embodiment of the implantable biosensor, the microacoustic sensor is connected to at least two electrodes that are placed in the measuring chamber in contact with the test fluid, wherein the sensor can detect electric conductivity of the test fluid by means of the two electrodes.

In the fourth embodiment of the biosensor according to the invention, it may be advantageous if it comprises a first chamber filled with the test fluid and a second chamber not filled with the test fluid, wherein the two electrodes connected to one of the reflectors of the microacoustic sensor are placed in the first chamber and the sensor is accommodated in the second chamber.

According to a second concept of the invention, a sensor arrangement for medical use is provided. The sensor arrangement comprises at least one implantable biosensor as described above and a reading or polling device, which is wirelessly coupled to the biosensor and in which the signals emitted by the biosensor are received and analyzed with respect to a determination of the concentration of the predetermined analyte or ion type. It may be preferable if the polling device is integrated in a medical or patient device. A "medical device" here and hereinafter shall be understood as a device by which a therapeutic benefit can be achieved, for example in that a therapeutic measure is proposed or carried out, such as the automatic dispensing of insulin for people with Diabetes mellitus. For this purpose, the medical device may be implanted in the body. However, it is also conceivable that the medical device is not implanted. It may furthermore be preferable if the medical or patient device is coupled to a home monitoring system for monitoring the concentrations of predetermined analytes or ion types of a patient.

BRIEF DESCRIPTION OF THE DRAWINGS

The invention will be explained in more detail based on exemplary embodiments, referencing the attached figures. Shown are.

DETAILED DESCRIPTION OF THE INVENTION

Figure 1:
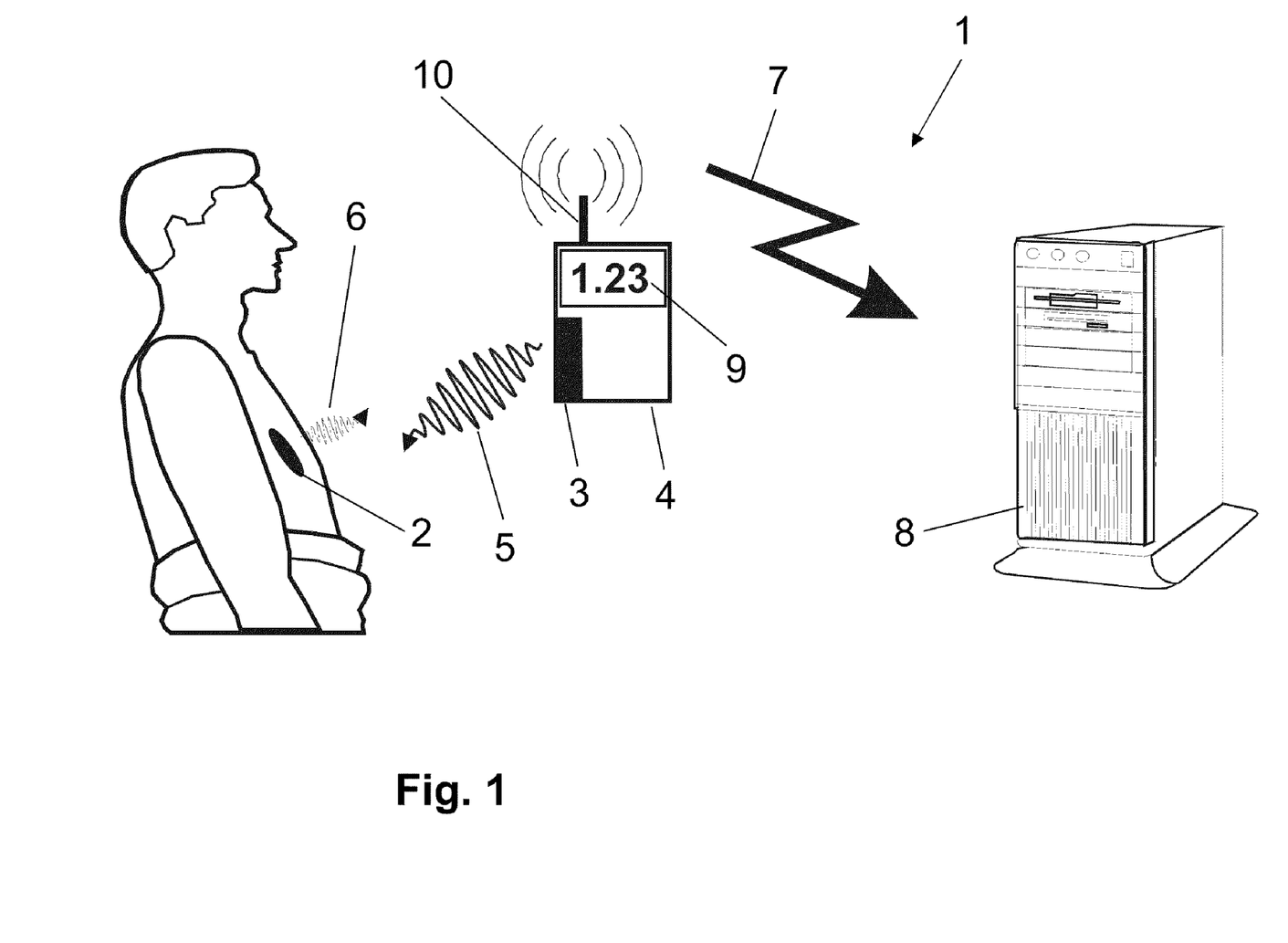
FIG. 1 is a schematic perspective view of an exemplary embodiment of the sensor arrangement according to the invention.

To begin with, FIG. 1 shall be discussed, which illustrates in a schematic perspective view one exemplary embodiment of the sensor arrangement according to the invention.

According to this figure, the sensor arrangement, which overall has been denoted with reference numeral 1, comprises a biosensor 2 implanted in the body of a patient, a device that can be wirelessly coupled to the biosensor 2, hereinafter referred to as "patient device" 4, which includes a polling unit 3 used to read the biosensor 2, and a home monitoring system 8 that can be coupled, for example wirelessly, to the patient device 4. The biosensor 2 comprises a test fluid accommodated in a measuring chamber, for example a hydrogel, which can respond to a change of the concentration of a predetermined analyte or an ion type with a physical change of state and which, for the detecting this change of state, is provided with at least one microacoustic sensor, for example a SAW sensor, as is explained in more detail based on the exemplary embodiments for the biosensor 2 illustrated in FIGS. 2 to 4.

The implanted biosensor 2 can be wirelessly polled by the polling unit 3 included in the patient device 4. As is shown by way of example in FIG. 1, the polling unit 3 may be located outside the body of the patient in the patient device 4. As an alternative, however, it is equally possible that the polling unit 3 is located in an external medical device (for example an insulin pump) or inside the body in a further implanted device (for example a pacemaker or an implanted preparation depot). Likewise, the biosensor 2 can be part of an implantable device, wherein then the polling of the microacoustic sensors or SAW sensors can also be carried out by wire.

The polling unit 3 comprises suitable means for transmitting a high-frequency electromagnetic pulse, hereinafter referred to as transmission pulse 5, for receiving the echo 6 reflected by the biosensor 2, and for signal processing and measured value calculation. As is shown in FIG. 1, the patient device 4 is equipped with a device antenna 10 for transmitting and receiving the electromagnetic pulses 5, 6.

Wireless polling of the biosensor 2 is carried out with the transmission pulse 5, which is modified by the SAW sensors in the biosensor 2 and is reflected as electromagnetic echo 6 ("SAW echo"). The polling unit 3 receives the SAW echo and, using generally known methods which do not need to be addressed in detail here, determines suitable parameters of the echoes and the concentrations of certain analytes or ions. For example, frequency shift, phase displacement, amplitude ratios, travel times, or decay time constants can be used as echo parameters that contain information about the concentrations of the analytes or ions to be measured.

The information about the concentrations of the analytes or ions can be used for managing a corresponding therapy or for monitoring the patient's state of health. The management of the therapy can be performed in an external medical device, or directly in an implanted medical device (IMD), or it is carried out via the external patient device 4, which includes the polling unit 3 and a unit for therapy management (not shown) and transmits therapy information via a communication connection to an implanted medical device.

In the exemplary embodiment shown in FIG. 1, the patient device 4 is connected to the home monitoring system 8, for example via a wireless communication connection 7. However, it would also be conceivable that the patient device 4 is connected to the home monitoring system 8 via a wired communication connection for data purposes.

The patient device 4 may comprise an input-output unit, such as a display 9, a membrane keyboard, and an acoustic signal transmitter. The information about the concentrations of analytes or ions can be indicated by the patient device 4 by way of the display 9. In addition, this information can be transmitted to the home monitoring system 8 via the communication connection 7.

The concentration information can be compared to suitable threshold values in the patient device 4 and/or in the home monitoring system 8 and, for example, based thereon alarms or therapy instructions can be generated. The comparison to the threshold values and the generation of the alarms or the therapy instructions can be carried out entirely or partially in the patient device 4 or in the home monitoring system 8, with or without the interaction of a physician.

Furthermore, the concentration information can be stored in the patient device 4 for a suitable time period and transmitted to the home monitoring system 8 at suitable times. Likewise, suitable parameters or trends can be determined from the concentration information, and in turn trend parameters can be determined from the trends. The determination of the parameters, trends and trend parameters can be carried out entirely or partially in the patient device 4 or in the home monitoring system 8. The parameters or the trend parameters can likewise be indicated in a suitable manner or be used for therapy management, or can be compared to threshold values, in order to generate alarms or therapy notes. This in turn can entirely or partially take place in the patient device 4 or in the home monitoring system 8.

Figure 2:
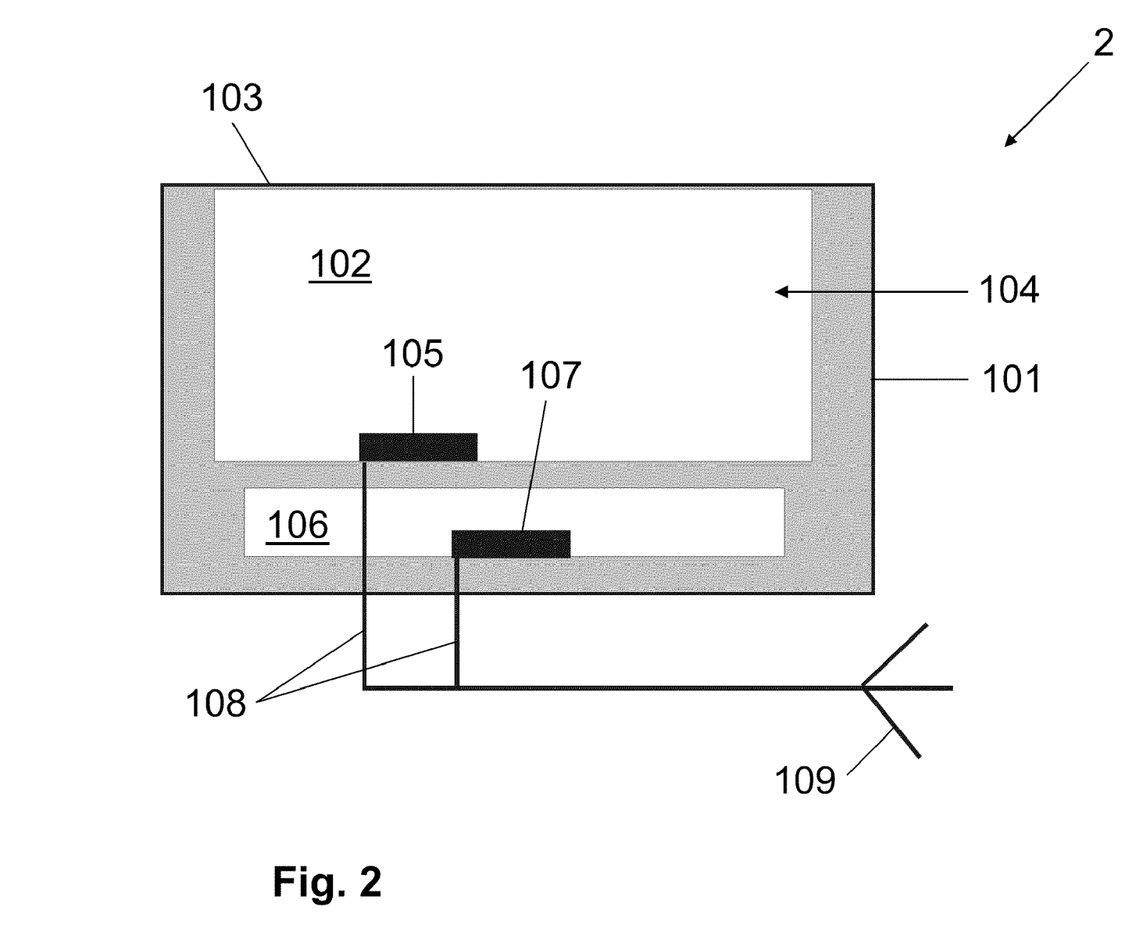
FIG. 2 is a schematic section illustration of a first exemplary embodiment of the biosensor according to the invention.

Reference is now made to FIG. 2, which shows a first exemplary embodiment of the biosensor 2 according to the invention of the sensor arrangement 1 based on a schematic section illustration.

The biosensor 2 is an implantable, wirelessly readable, passive sensor, which can be used primarily for determining the glucose content in the blood or in connective tissue fluid. The biosensor 2 is implanted in a suitable location, for example under the skin. It comprises a capsule 101, which is made of a suitable biocompatible material and surrounds a measuring chamber or first chamber 102. On one side, the capsule 101 or first chamber 102 is closed by a suitable semi-permeable membrane 103. The first chamber 102 of the capsule 101 is filled with a suitable test fluid 104 or hydrogel, for example with a solution comprising dextran and concanavalin A, wherein the test fluid 104 has the attribute that it can change the viscosity thereof as a function of the glucose concentration. The membrane 103 is configured such that it allows glucose molecules to pass and at the same time prevents test fluid 104 from escaping, so that a balance of the glucose concentration forms between the test fluid 104 in the first chamber 102 and the surrounding bodily fluid. A change of the glucose concentration in the test fluid 104 results in a change of the viscosity thereof. As a result, the glucose concentration in the bodily fluid can be determined by determining the viscosity of the test fluid 104.

The viscosity of the test fluid 104 is determined by way of a first SAW sensor 105, which is provided in a suitable location in the first chamber 102 of the capsule 101 such that the sensitive surface thereof is in contact with the test fluid 104, the propagation of the acoustic waves on the sensitive surface being influenced by the viscosity of the test fluid 104.

A second SAW sensor 107 is provided such that the sensitive surface thereof has no contact with the test fluid 104. As FIG. 2 shows by way of example, the second SAW sensor 107 for this purpose is accommodated in an additional, enclosed, preferably evacuated second chamber 106. The wave propagation on the sensitive surface of the second SAW sensor 107 is therefore only influenced by the temperature and serves for the passive wireless temperature measurement for the temperature correction of the viscosity measurement of the first SAW sensor 105.

Both SAW sensors 105, 107 are connected to one or more suitable sensor antennas 109 by way of appropriate cables 108. This sensor antenna 109 is used, or these sensor antennas are used, to couple the transmission pulse 5 of the polling unit 3 and reflect the echo 6 of the two SAW sensors 105, 107 in order to be received by the evaluation or polling unit 3 and processed. Through a suitable design of the two SAW sensors 105, 107, for example through different resonant frequencies, it is possible to associate the echoes 6 received with the corresponding SAW sensors 105, 107.

The evaluation or polling unit 3, which, for example, is part of the external medical or patient device 4, such as an insulin pump, transmits one or more transmission pulses 5 and receives the echo or echoes 6 from the implanted biosensor 2. At least one echo 6 contains the information about the viscosity of the test fluid 104 and at least one echo 6 contains the temperature information. The polling unit 3 determines this information from the properties of the echo 6, for example by a determination of the shift of the echo frequencies, generates a measured value for the viscosity and a value for the temperature, and performs a temperature correction of the measured viscosity value. From the temperature-corrected measured viscosity value then the glucose concentration in the bodily fluid is determined by way of the correlation between viscosity and glucose concentration and transmitted to the medical or patient device 4 for further use. This polling can be carried out cyclically, for example every 5 minutes, at certain intervals, or in certain time periods (for example in the morning, at lunch time, in the evening and at midnight). The medical or patient device 4 uses the glucose concentration values to determine the necessary therapy parameters, for example the insulin administration dosage. The measured glucose concentration can be indicated on the display 9 of the medical or patient device 4, stored in the patient device 4, and transmitted to the home monitoring system 8 via the communication connection 7. The glucose concentrations allow trends and trend parameters to be determined in the patient device 4 or in the home monitoring system 8, which can then again be indicated on the display 9 of the patient device 4. It is also possible to compare the glucose concentrations or the trend parameters in the patient device 4 or in the home monitoring system 8 to suitable threshold values and to generate alarm messages. The glucose values and trends can also be used for monitoring the course of the disease or the therapy by the patient or the treating physician, for example the adherence to a certain diet.

Figure 3:
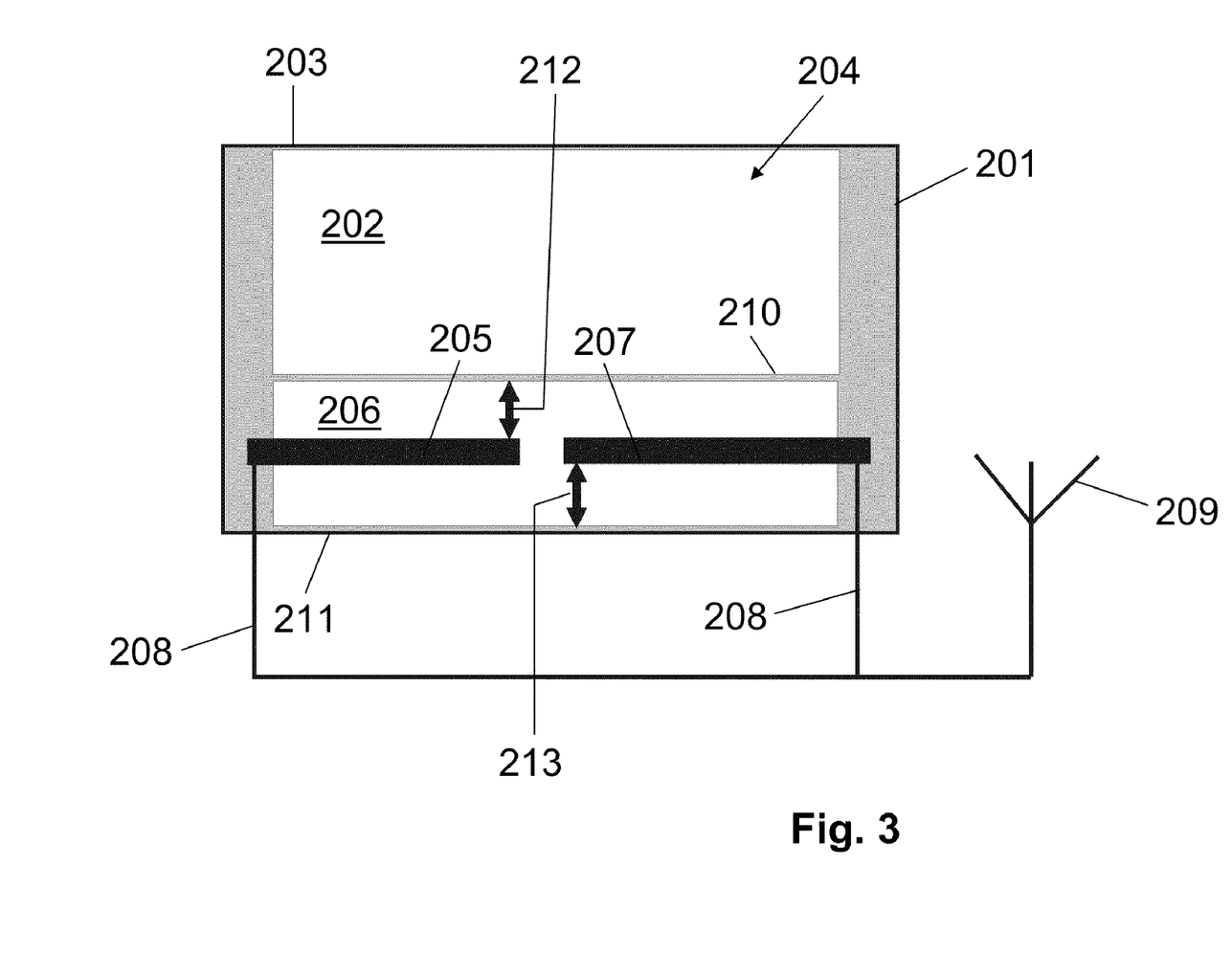
FIG. 3 is a schematic section illustration of a second exemplary embodiment of the biosensor according to the invention.

Reference is now made to FIG. 3, which shows a second exemplary embodiment of the biosensor 2 according to the invention of the sensor arrangement 1 based on a schematic section illustration.

The biosensor 2 is an implantable, wirelessly readable, passive sensor, which can be used primarily for determining the glucose content in the blood or in connective tissue fluid. The biosensor 2 is implanted in a suitable location, for example in the tissue. It comprises a capsule 201, which is made of a suitable biocompatible material and surrounds a measuring chamber or first chamber 202. On one side, the capsule 201 or first chamber 202 is closed by a suitable semi-permeable, rigid membrane 203. The first chamber 202 of the capsule 201 is filled with a suitable test fluid 204, for example with a mixture of a suitable polymer and concanavalin A as a glucose-binding molecule, wherein the test fluid 204 has the attribute that it can change the volume thereof as a function of the glucose concentration, which is to say to swell or to shrink. The membrane 203 is configured such that it allows glucose molecules to pass and at the same time prevents test fluid 204 from escaping, so that a balance of the glucose concentration forms between the test fluid 204 in the capsule 201 and the surrounding bodily fluid. The test fluid 204 swells or shrinks as a function of the glucose concentration, thereby resulting in pressure changes in the first chamber 202. When using a suitable test fluid 204 these pressure changes can also be caused by osmotic pressure, which likewise depends on the glucose concentration. In this way, the measurement of the pressure difference between the first chamber 202 and the surrounding area can be used to determine the glucose content in the bodily fluid.

A measurement of the pressure difference is carried out with microacoustic sensors, for example SAW sensors 205, 207. A first SAW sensor 205 is used to measure the pressure in the first chamber 202, and a second SAW sensor 207 is used to measure the ambient pressure outside the biosensor 2. A further SAW sensor (not shown) can be suitably disposed in order to additionally determine the temperature of the arrangement such that by the temperature detected the temperature dependence of the two SAW sensors 205, 207 and the thermal expansion in the measurement arrangement can be compensated for, if necessary. The two SAW sensors 205, 207 are connected to one or more suitable sensor antennas 209 by way of appropriate cables 208. This sensor antenna 209 is used, or these sensor antennas are used, to couple the transmission pulse 5 of the polling unit 3 and reflect the echo 6 of the two SAW sensors 205, 207 in order to be received by the evaluation or polling unit 3. Through a suitable design of the two SAW sensors 205, 207, for example through different resonant frequencies, it is possible to associate the echo 6 received with the corresponding SAW sensors 205, 207.

For this purpose, the first chamber 202 filled with the test fluid 204 is closed, for example on one side, by a first, hermetically sealed pressure measuring membrane 210, onto which the pressure in the first chamber 202 acts. Behind it, a second, for example evacuated, chamber 206 is located. The two SAW sensors 205, 207 for the pressure measurement, and optionally another for the temperature measurement, are disposed in this second chamber 206. This second chamber 206 is closed to the outside by a second, hermetically sealed pressure measuring membrane 211, onto which the ambient pressure acts.

The two SAW sensor 205, 207 each are configured, for example, as a bending beam, the one end of which is fixed in the wall of the capsule 201 and the other end is freely suspended. Using suitable first or second tappets 212, 213, a pressure-dependent deformation of the associated pressure measuring membranes 210, 211 is transmitted to the freely suspended ends of the two SAW sensors 205, 207, whereby the SAW sensors 205, 207 are slightly deflected. This slight deflection results in mechanical stresses in the SAW sensors 205, 207, whereby the propagation properties of the acoustic waves on the surfaces thereof are influenced, for example the propagation velocities thereof.

Figure 3A:
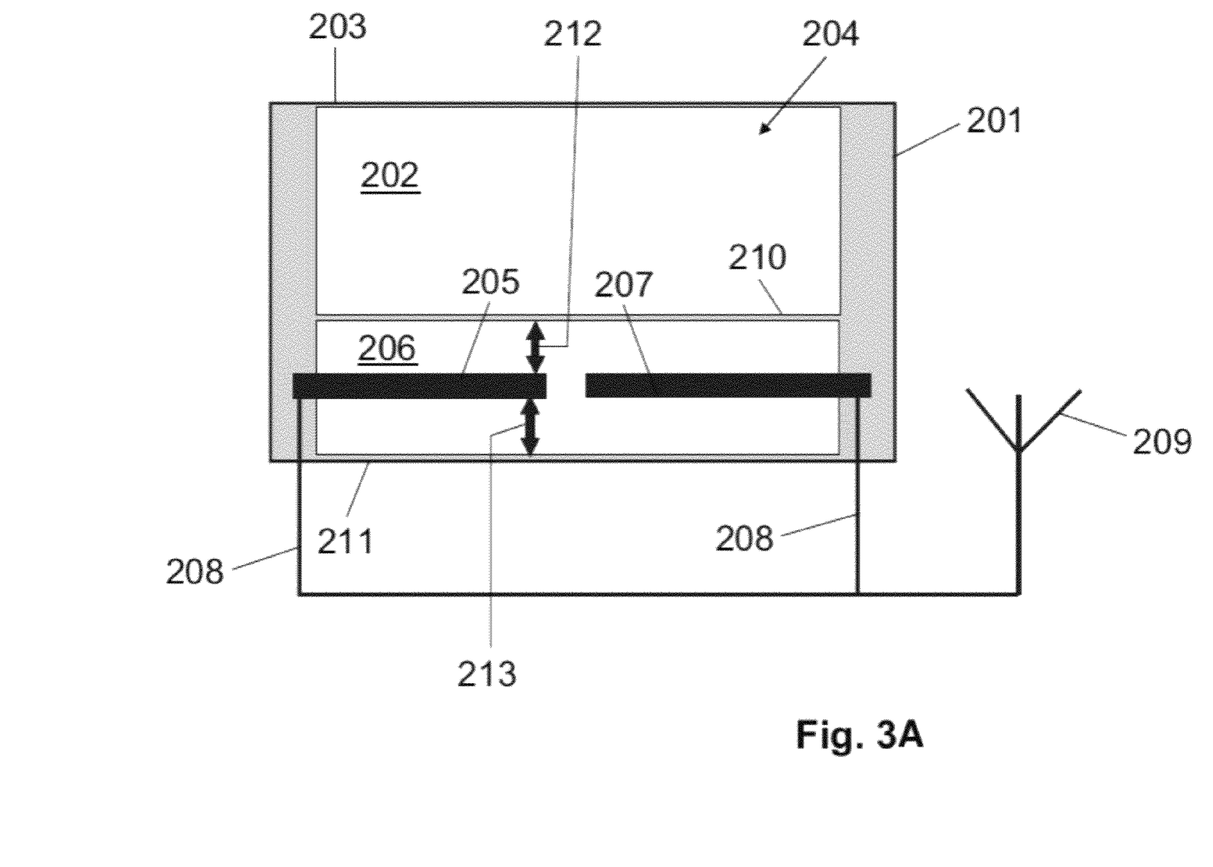
FIG. 3A is a schematic section illustration of an alternate second exemplary embodiment of the biosensor according to the invention.

The special arrangement according to FIG. 3 of course serves only illustration purposes, and another arrangement, by which the pressure difference between the first chamber 202 and the surrounding area can be measured, can likewise be used. For example, the second tappet 213, which transmits the ambient pressure, can likewise be guided to the end of the first SAW sensor 205, thereby causing the deflection of this SAW sensor 205 directly by the pressure difference. This is shown in FIG. 3A. The second SAW sensor 207 can then be used for temperature measurement. The temperature measurement, for example, can also be made possible in that several reflectors are attached in suitable positions on the two SAW sensors 205, 207.

In principle, other pressure pickups, for example capacitive or piezoresistive pressure sensors, can also be used for measuring the pressure in the first chamber 202 and the ambient pressure, wherein pressures changes result in a change of the impedance of these sensors. These pressure pickups are connected to the ports of suitable reflectors on the surfaces of the two SAW sensors 205, 207 such that the impedance changes thereof result in a change of the reflection properties of the reflectors.

The evaluation or polling unit 3, which here, for example, is part of an implanted medical device (such as an implanted insulin depot), transmits one or more transmission pulses 5 and receives the echo or echoes 6 from the implanted biosensor 2. At least one echo 6 contains the information about the pressure in the first chamber 202, and at least one echo contains the information about the ambient pressure. The polling unit 3 determines this information from the properties of the echoes 6, for example by way of a determination of the travel times of the echoes 6, and in each case generates a measured value for the pressure in the first chamber 202 and a value for the ambient pressure. The difference of the two measured pressure values, which can undergo a temperature correction, is used to suitably determine the glucose content in the bodily fluid. The polling of the biosensor 2 can be carried out cyclically or at certain times. Based on the measured glucose values, the implanted insulin depot controls the dosage of the insulin that is dispensed, for example. Due to the continuous glucose measurement, which is possible due to the biosensor 2 according to the invention, a closed loop for insulin dosing can be implemented.

The measured glucose values can be stored in the implanted medical device (IMD), or they can be transmitted via a suitable communication connection to the external patient device 4 and from there to the home monitoring system 8. From the measured glucose values, parameters can be determined entirely or partially in the implanted medical device (IMD), in the patient device 4, or in the home monitoring system 8, or trends and trend parameters can be determined It is also possible to compare the glucose concentrations or the trend parameters in the implanted medical device (IMD), in the patient device 4, or in the home monitoring system 8, entirely or partially to suitable threshold values and to generate alarm messages. The glucose values and trends can also be used for monitoring the course of the disease or the therapy by the patient or the treating physician, for example the adherence to a certain diet.

Figure 4:
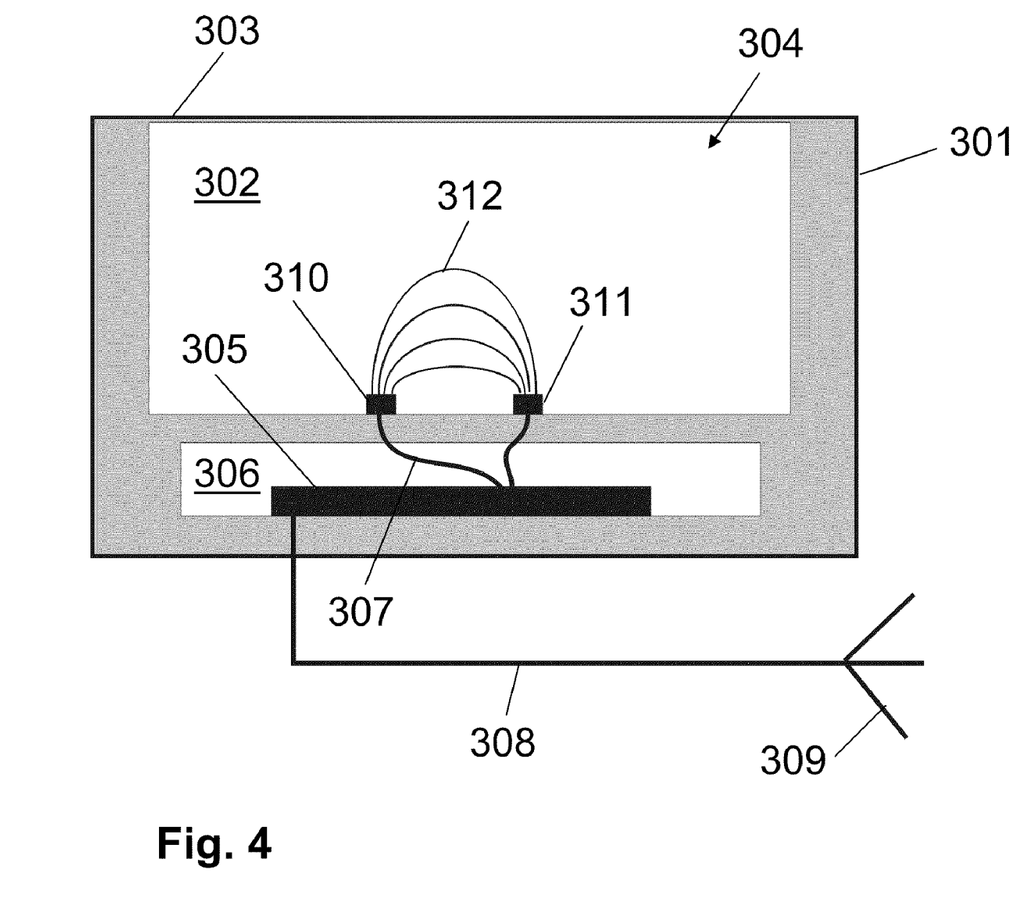
FIG. 4 is a schematic section illustration of a third exemplary embodiment of the biosensor according to the invention.

Reference is now made to FIG. 4, which shows a third exemplary embodiment of the biosensor 2 according to the invention of the sensor arrangement 1 based on a schematic section illustration.

The biosensor 2 is an implantable, wirelessly readable, passive sensor, which can be used primarily for determining the glucose content in the blood or in connective tissue fluid. The biosensor 2 is implanted in a suitable location, for example in a blood vessel. It comprises a capsule 301, which is made of a suitable biocompatible material and surrounds a measuring chamber or first chamber 302. On one side, the capsule 301 or first chamber 302 is closed by a suitable semi-permeable membrane 303. The first chamber 302 of the capsule 301 is filled with a suitable test fluid 304, for example with a mixture of a suitable polymer and concanavalin A as a glucose-binding molecule, wherein the test fluid 304 has the attribute that it can change the electrical properties thereof, such as conductivity or permittivity, selectively as a function of the pH value. The membrane 303 is configured such that it allows hydrogen ions to pass and at the same time prevents test fluid 304 from escaping, so that a balance of hydrogen ions forms between the test fluid 304 in the capsule 301 and the surrounding bodily fluid. In this way, the pH value in the blood can be determined by way of a conductivity measurement in the first chamber 302. The measurement of conductivity is carried out by means of a microacoustic sensor, for example a SAW sensor 305. For this purpose, the first chamber 302 comprises suitably arranged first and second electrodes 310, 311, which can be configured, for example, as interdigital electrodes, so that the electric stray field 312 between these electrodes 310, 311 extends sufficiently far into the test fluid 304. The two electrodes 310, 311 are connected to the ports of a suitable reflector on the SAW sensor 305 by way of appropriate first cables 307. The AC voltage impedance between the two electrodes 310, 311 with the real and imaginary parts ($Z=R+jX$) thereof influences the reflection properties of the reflector connected to them and provided on the SAW sensor 305 with respect to the magnitude and phase.

In addition, the SAW sensor 305 comprises at least one further reflector, which enables a temperature measurement and temperature correction. The temperature detected can be used to compensate for the temperature dependence of the SAW sensor 305 and that of the electric properties of the test fluid 304. The SAW sensor 305 is connected to one or more suitable sensor antennas 309 by way of a second cable 308. This sensor antenna 309 is used, or these sensor antennas are used, to couple the transmission pulse 5 of the polling unit 3 and reflect the echo 6 of the SAW sensor 305 in order to be received by the evaluation or polling unit 3.

The evaluation or polling unit 3, which here, for example, is part of the external patient device 4, transmits one or more transmission pulses 5 and receives the echoes 6 from the implanted biosensor 2. At least one echo 6 contains the information about the conductivity of the test fluid 304 and at least one echo 6 contains the temperature information. The polling unit 3 determines this information from the properties of the echoes 6, for example by a determination of the amplitudes and phasings of the echoes 6, generates a measured value for the conductivity and a value for the temperature, and performs a temperature correction of the measured conductivity value. The temperature-corrected measured conductivity value is then used to determine the pH value in the blood based on the correlation between the conductivity of the test fluid 304 and the pH value. This polling can be carried out cyclically, for example every 5 minutes, at certain intervals, or in certain time periods, or as a function of the patient's physical activity. Based on the measured values for the pH value, the patient device 4 can initiate the necessary therapeutic measures, indicate the measured pH value on the display 9 or store the pH values, and transmit them to the home monitoring system 8 via the communication connection 7. The pH values allow trends and trend parameters to be determined in the medical or patient device 4 or in the home monitoring system 8, which can then again be indicated on the display 9 of the medical or patient device 4. It is also possible to compare the pH values or the trend parameters in the medical or patient device 4, or in the home monitoring system 8, to suitable threshold values and to generate alarm messages. The pH values and trends can also be used for monitoring the course of the disease or the therapy by the patient or the treating physician.

The invention describes implantable, wirelessly readable, non-battery operated biosensors for measuring the concentration of an analyte (for example glucose, biomarkers, hormones, enzymes, or proteins) or an ion type (for example pH value or calcium ions) in an aqueous solution (for example in the blood or in connective tissue fluid). The biosensors according to the invention operate based on a test fluid, for example hydrogels of the known types, and utilize the known changes in the physical parameters thereof, such as volume changes, viscosity changes, or changes of the electric and dielectric properties, as a function of the concentration of the analyte or ion type. The biosensors comprise a suitably configured measuring chamber, which contains a test fluid that is suited for measuring the concentration of the analyte or ion type, for example a hydrogel. This measuring chamber is closed on at least one surface by a suitable semi-permeable membrane, which allows the analyte or ion type to pass into the measuring chamber and reliably prevents the test fluid or measuring solution from escaping. In this way, a concentration balance of the analyte builds between the surrounding area and the interior of the measuring chamber.

In contrast to known apparatuses, the changes of the physical parameters of the test fluid or hydrogels are measured using purely passively operating SAW sensors, which can be polled wirelessly. This has the advantage that the biosensors according to the invention need no measuring electronics and no apparatuses for active telemetry, thereby requiring no batteries or other energy accumulators.

The SAW sensors employed in the biosensor according to the invention can be configured as delay lines or as one-port resonators. The suitable range for the resonant frequency of the SAW sensor is approximately 30 MHz to approximately 10 GHz, wherein frequencies in the ISM band (433 MHz) or in the MICS band (402-405 MHz) are preferred for implantable sensors. Since the properties of the SAW sensors are also influenced by the temperature, the biosensors according to the invention use one or more SAW sensors, wherein at least one has no effective contact with the measuring medium and is suitably used for temperature compensation or temperature measurement. It is also possible to use at least one SAW sensor having at least two reflectors, wherein at least one of the reflectors is used to generate signals for temperature measurement or temperature compensation.

For biosensors that utilize a volume change of the test fluid, for example a hydrogel, or a change of the osmotic pressure as a function of the concentration of the analyte or ion type, the SAW sensors used for pressure measurement may be disposed such that at least one determines the pressure in the measuring chamber, while at least one other determines the ambient pressure outside the measuring chamber. The difference of the two pressures then corresponds to the pressure built in the measuring chamber as a result of the swelling of the test fluid, for example the hydrogel, or by osmosis, from which the concentration of the analyte or ion type is determined. The use of these two measured values additionally enables temperature compensation.

For biosensors that utilize the viscosity change of the hydrogels as a function of the concentration of the analyte or ion type, the temperature measurement with the SAW sensor used therefor can also be used to compensate not only for the temperature dependence of the SAW sensors, but also for the temperature dependence of the viscosity of the test fluid, for example the hydrogel, or the measuring solution.

LIST OF REFERENCE NUMERALS

1 Sensor arrangement
2 Biosensor
3 Polling unit
4 Patient device
5 Transmission pulse
6 Echo
7 Communication connection
8 Home monitoring system
9 Display
10 Device antenna
101 Capsule
102 First chamber
103 Membrane
104 Test fluid
105 First SAW sensor
106 Second chamber
107 Second SAW sensor
108 Cable
109 Sensor antenna
201 Capsule
202 First chamber
203 Membrane
204 Test fluid
205 First SAW sensor
206 Second chamber
207 Second SAW sensor
208 Cable
209 Sensor antenna
210 First pressure measuring membrane
211 Second pressure measuring membrane
212 First tappet
213 Second tappet
301 Capsule
302 First chamber
303 Membrane
304 Test fluid
305 SAW sensor
306 Second chamber
307 First cable
308 Second cable
309 Sensor antenna
310 First electrode
311 Second electrode
312 Electric stray field

What is claimed is:

1. An implantable biosensor (2) comprising:
a test fluid (104; 204; 304);
a first chamber (102; 202; 302) filled with the test fluid (104; 204; 304);
wherein the test fluid (104; 204; 304) is configured to convert a change of a concentration of a predetermined analyte or ion type into a change of a physical variable;
at least one membrane (103; 203; 303);
wherein the first chamber (102; 202; 302) is closed by the at least one membrane (103; 203; 303);
wherein the at least one membrane (103; 203; 303) is permeable to the predetermined analyte or ion type and impermeable to the test fluid (104; 204; 304);
an antenna;
at least one microacoustic sensor (105, 107; 205, 207; 305), which is operatively connected to the test fluid (104; 204; 304) such that it can detect the change of the physical variable that changes with the change of the concentration of the predetermined analyte or ion type wherein said at least one microacoustic sensor is coupled with said antenna and is passive and obtains power via said antenna and wherein said at least one microacoustic sensor comprises a respective resonant frequency and wherein said at least one microacoustic sensor receives a transmission pulse (5) at said respective resonant frequency which is modified by said at least one microacoustic sensor and reflected via said antenna as an electromagnetic echo (6);
a second chamber (206) not filled with the test fluid (204);
a first pressure measuring membrane (210);
wherein the first chamber (202) and said second chamber (206) are separated from each other at least in some sections by the first pressure measuring membrane (210) wherein said first pressure measuring membrane (210) is configured to deform in an event of a pressure difference between said first chamber (202) and said second chamber (206);
a second pressure measuring membrane (211);
wherein the second chamber (206) is separated from a surrounding area at least in some sections by the second pressure measuring membrane (211) that is configured to deform in an event of a pressure difference of the second chamber (206) relative to the surrounding area;
a microacoustic sensor (205) selected from the at least one microacoustic sensor (105, 107; 205, 207; 305) wherein said microacoustic sensor (205) is accommodated in the second chamber (206); and,
wherein the microacoustic sensor (205) is operatively connected to the first and second pressure measuring membranes (210, 211) such that the microacoustic sensor (205) is configured to detect deformations thereof.

2. The implantable biosensor (2) according to claim 1, wherein the microacoustic sensor (205) is configured as a bendable element that is mechanically coupled to the first and/or second pressure measuring membrane (210, 211).

3. An implantable biosensor (2) according to claim 1, further comprising:
a further microacoustic sensor accommodated in the second chamber (206) and configured to detect temperature.

4. An implantable biosensor (2) according to claim 1, wherein the test fluid (204) is configured to convert the change of the concentration of an analyte or ion type into a change of a volume of the test fluid.

5. An implantable biosensor (2) according to claim 1, wherein the test fluid (204) is configured to convert the change of the concentration of glucose or ion type into a change of a volume of the test fluid.

* * * * *